US012685795B1

(12) United States Patent
Brown

(10) Patent No.: US 12,685,795 B1
(45) Date of Patent: Jul. 21, 2026

(54) VAGIPLUG

(71) Applicant: Teneha G. Brown, New Orleans, LA (US)

(72) Inventor: Teneha G. Brown, New Orleans, LA (US)

( * ) Notice: Subject to any disclaimer, the term of this patent is extended or adjusted under 35 U.S.C. 154(b) by 937 days.

(21) Appl. No.: 16/508,116

(22) Filed: Jul. 10, 2019

Related U.S. Application Data

(60) Provisional application No. 62/695,844, filed on Jul. 10, 2018.

(51) Int. Cl.

| | |
|---|---|
| *A61L 2/26* | (2006.01) |
| *A61F 6/12* | (2006.01) |
| *A61L 103/05* | (2026.01) |

(52) U.S. Cl.
CPC . *A61L 2/26* (2013.01); *A61F 6/12* (2013.01); *A61L 2103/05* (2026.01)

(58) Field of Classification Search
CPC ..................................... A61F 6/12; A61F 6/08
See application file for complete search history.

(56) References Cited

U.S. PATENT DOCUMENTS

| | | | |
|---|---|---|---|
| 4,209,009 A | | 6/1980 | Hennig |
| 4,241,912 A | * | 12/1980 | Mercer .................. A63B 23/20 |
| | | | 606/191 |
| 4,349,031 A | | 9/1982 | Perlin |
| 4,515,167 A | | 5/1985 | Hochman |
| 4,785,828 A | | 11/1988 | Maurer |
| 4,922,928 A | | 5/1990 | Burnhill |
| 7,077,826 B1 | * | 7/2006 | Gray ................... A61M 5/3137 |
| | | | 604/212 |
| 8,217,219 B2 | | 7/2012 | Shepard et al. |
| 9,445,882 B2 | | 9/2016 | Henriksson |
| 2003/0060785 A1 | | 3/2003 | Lavean et al. |
| 2004/0230183 A1 | * | 11/2004 | Breegi .................. A61F 9/0017 |
| | | | 604/891.1 |

| | | | |
|---|---|---|---|
| 2005/0256483 A1 | | 11/2005 | Przepasniak et al. |
| 2008/0125692 A1 | * | 5/2008 | Feemster .................. A61F 6/08 |
| | | | 604/15 |
| 2009/0005635 A1 | | 1/2009 | Zhang et al. |
| 2013/0138134 A1 | * | 5/2013 | Elman ............... A61M 25/0026 |
| | | | 606/193 |
| 2015/0305844 A1 | | 10/2015 | Schuman et al. |
| 2015/0320587 A1 | | 11/2015 | Coker |
| 2016/0106465 A1 | * | 4/2016 | Richey ............... A61B 17/0482 |
| | | | 600/37 |
| 2017/0238768 A1 | * | 8/2017 | Schull .................... A47K 7/028 |
| 2018/0311441 A1 | * | 11/2018 | Cave .................. A61M 5/31511 |

FOREIGN PATENT DOCUMENTS

| | | |
|---|---|---|
| JP | 2016524511 | 8/2016 |
| WO | 2004071372 | 8/2004 |
| WO | 2005110316 | 11/2005 |
| WO | 2014165477 | 10/2014 |

OTHER PUBLICATIONS

Merriam-Webster, Frustum definition, 1 pgs.*
Dictionary.com, 'ridge', 1 page.*
ThinkMax Women Rose Essential Oil Vagina Tightening Device, Sep. 28, 2018; Amazon.com.
Vibrating Smart Kegel Exercise Balls Vaginal Trainer, Sep. 28, 2018; Amazon.com.
New Kegel Vaginal Balls for Women, Sep. 28, 2018; Amazon.com.
Woman Vaginal Vibrator 10 Speeds Anal Plug Vibrator, Sep. 28, 2018; Amazon.com.

* cited by examiner

*Primary Examiner* — Kyle A Purdy
(74) *Attorney, Agent, or Firm* — Garvey, Smith & Nehrbass, Patent Attorneys, L.L.C.; Julie Rabalais Chauvin; Vanessa M. D'Souza

(57) ABSTRACT

A method and device provide vaginal protection from entrance of substances and includes a device for insertion into the human vagina/vaginal canal to prevent unintentional entry of substance of materials into the vagina/vaginal canal such as soaps, irritants, waxes in the case of bikini waxing and specifically Brazilian waxing procedure, pubic hair removal creams/lotions and the like, that may initiate or foster regional infections etc. The method and device also serve to block odors when inside the vagina/vaginal canal.

18 Claims, 6 Drawing Sheets

30

VAGIPLUG

CROSS-REFERENCE TO RELATED APPLICATIONS

This application claims the benefit of my U.S. Provisional Patent Application Ser. No. 62/695,844, filed 10 Jul. 2018, which is hereby incorporated herein by reference.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to a method and device for vaginal protection from entrance of substances (i.e. soaps, irritants, bodywash and the like) that may or may not interfere with vaginal pH (acidic or basic center inside the vagina; acidic or basic flora levels) thereby impacting the natural vaginal flora in a manner that may or may not cause vaginal infections, bacterial infections and the like.

2. General Background of the Invention

The present invention relates to a method and device for vaginal protection from entrance of substances (i.e. soaps, irritants, bodywash and the like) that may or may not interfere with vaginal pH (acidic or basic center inside the vagina; acidic or basic flora levels) thereby impacting the natural vaginal flora in a manner that may or may not cause vaginal infections, bacterial infections and the like. Other devices have been made for use in the vagina/vaginal canal for other purposes, such as for menses, the introduction of medicine(s), and for contraception.

The following possibly relevant US Patents are each hereby incorporated herein by reference:

BRIEF SUMMARY OF THE INVENTION

The present invention relates to a method and device for vaginal protection from entrance of substances (i.e. soaps, irritants, bodywash and the like) that may or may not interfere with vaginal pH (acidic or basic center inside the vagina: acidic or basic flora levels) thereby impacting the natural vaginal flora in a manner that may or may not cause vaginal infections, bacterial infections and the like.

The present invention relates to a device for insertion into the human vagina/vaginal canal to prevent unintentional entry of substance of materials into the vagina/vaginal canal such as soaps, irritants, waxes in the case of bikini waxing and specifically Brazilian waxing procedure around the vaginal area/crotch, pubic hair removal creams/lotions and the like, that may initiate or foster regional infections etc. The present invention relates to a device can also function as an odor blocker when inside the vagina/vaginal canal. The present invention relates to a device that can be temporarily inserted into the vagina to prevent the entry of foreign substances therein and protect the vagina from infection.

One objective of the present invention is to prevent entry of substances albeit foreign or non-foreign into the vagina/vaginal canal that may or may not have an impact on the natural vaginal flora, thereby possibly inducing vaginal infection or bacterial infection and the like. In various preferred embodiments of the present invention, the present invention includes a tube that is inserted into the vagina/vaginal canal that preferably serves to prevent fluids or materials (soaps, perfumed soaps, perfumed body washes, body washes, waxes and the like) from entering the vagina/vaginal canal. The tube can be solid or hollow or partially solid and partially hollow. In a preferred embodiment, the tube is the approximate length and width of the vagina/vaginal canal necessary to provide a snug fit but not too snug to cause irritation and non-functionality. In a preferred embodiment, the tube extends vertically from just below the cervix and extends just outside the opening of the vagina. In a preferred embodiment, the present invention includes a tip at the end of the tube that aids in insertion into and removal from the vagina. The tip can also be used to adjust the present invention once inserted into the vagina. In a preferred embodiment, the tip extends just beyond the vaginal

| Pat. No. | Title | Issue Date MM-DD-YYYY |
|---|---|---|
| 4,209,009 | Anus Closure Tampon And Method Of Manufacture | Jun. 24, 1980 |
| 4,785,828 | Vaginal Stimulator For Controlling Urinary Incontinence In Women | Nov. 22, 1988 |
| 4,515,167 | Device For The Development, Training And Rehabilitation Of The Pubococcygeal And Related Perineal Musculature Of The Female | May 7, 1985 |
| 4,349,031 | Esophageal Probe With Disposable Cover | Sep. 14, 1982 |
| 4,922,928 | Vaginal Device | May 8, 1990 |
| 8,217,219 | Anatomically Conforming Vaginal Insert | Jul. 10, 2012 |
| 9,445,882 | Vaginal Device | Sep. 20, 2016 |
| 2003/0060785 | Disposable Vaginal Device | Mar. 27, 2003 |
| 2005/0256483 | Disposable Vaginal Insertion Device | Nov. 17, 2005 |
| 2009/0005635 | Disposable Device For Vaginal Cleaning And Hygiene | Jan. 1, 2009 |
| 2015/0305844 | Vaginal Insert | Oct. 29, 2015 |
| 2015/0320587 | Vaginal Protector | Nov. 12, 2015 |
| WO 2004/071372 | Vagina Stimulator | Aug. 26, 2004 |
| WO 2005/110316 | Disposable Device For Mechanically Engaging A Vagina | Nov. 24, 2005 |
| WO 2014/165477 | Anatomic Vaginal Occluder | Oct. 9, 2014 |
| JP 2016524511 | Vaginal Insertion Assembly | Aug. 18, 2016 |

3 opening and is preferably pyramidical in shape. In a preferred embodiment, the tip of the present invention protrudes just a bit beyond the vaginal opening, but not to the point of obstruction or causing irritation. Additionally, the present invention can be used during a pubic hair removal process from around the vaginal area otherwise known as bikini waxing or Brazilian waxing or a similar procedure. Use of the present invention during a bikini waxing or similar procedure preferably prevents the waxing solution, cream or other products used during hair removal procedure from getting into the vagina/vaginal canal. Furthermore, the present invention can also preferably be used as an odor blocker if a vaginal or bacterial infection has already begun in the canal. The present invention can preferably be inserted and used as plug to prevent odors from polluting from the vagina/vaginal canal/vaginal area due to vaginal or bacterial infection and the like.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Figure 1:
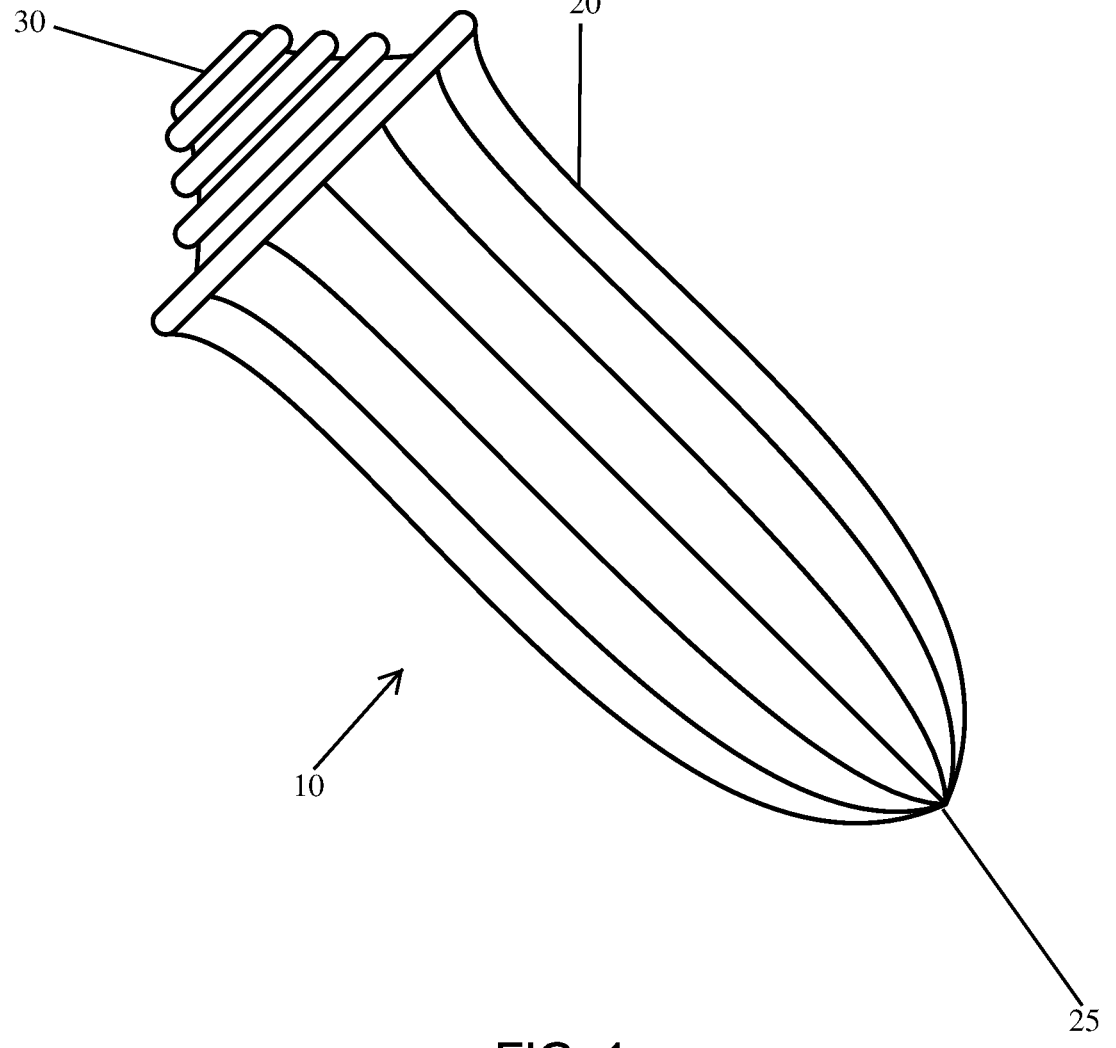
FIG. 1 is a lateral view of a preferred embodiment of the present invention.
Figure 5:
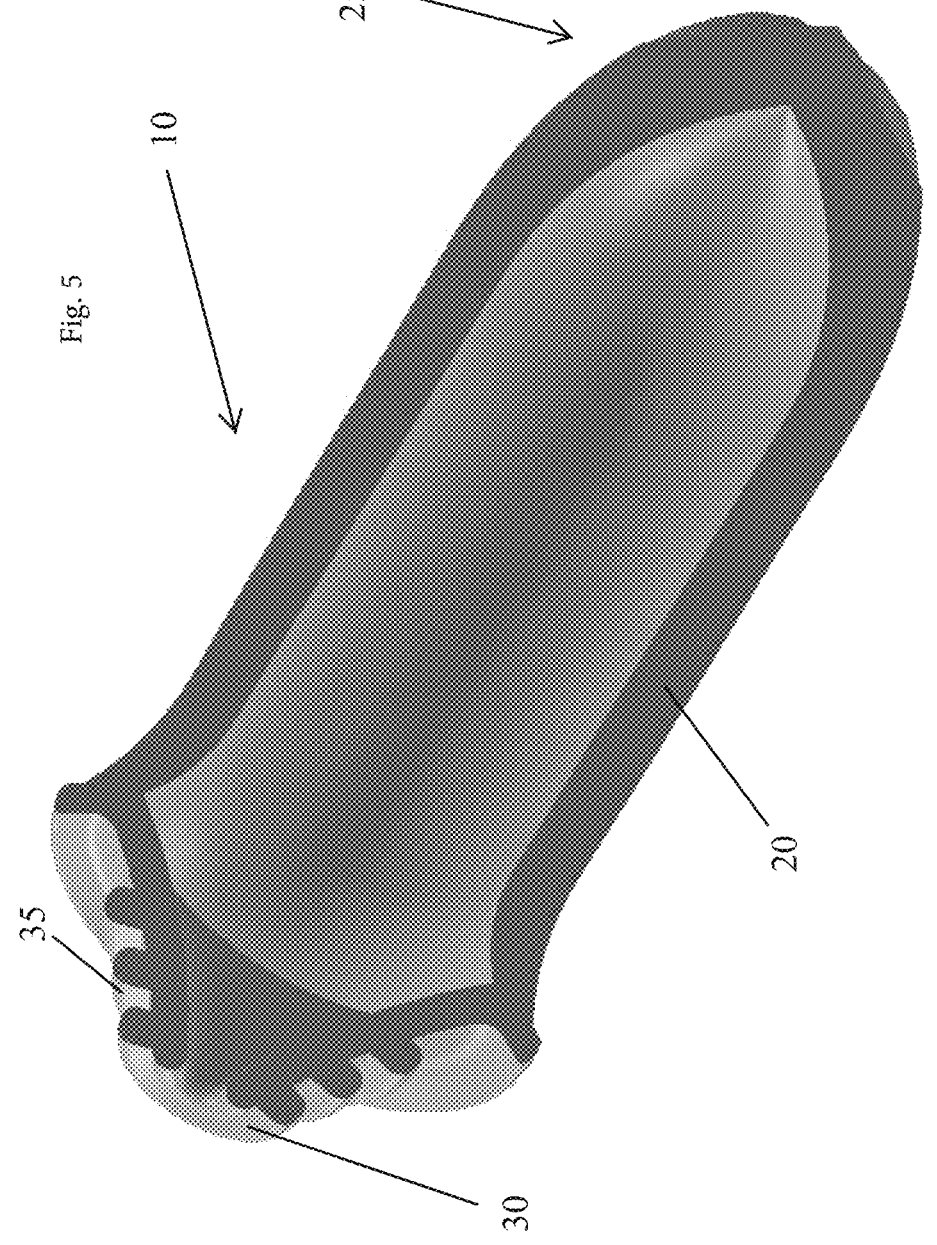
FIG. 5 is a cross-section view of a preferred embodiment of the device of the present invention.
Figure 6:
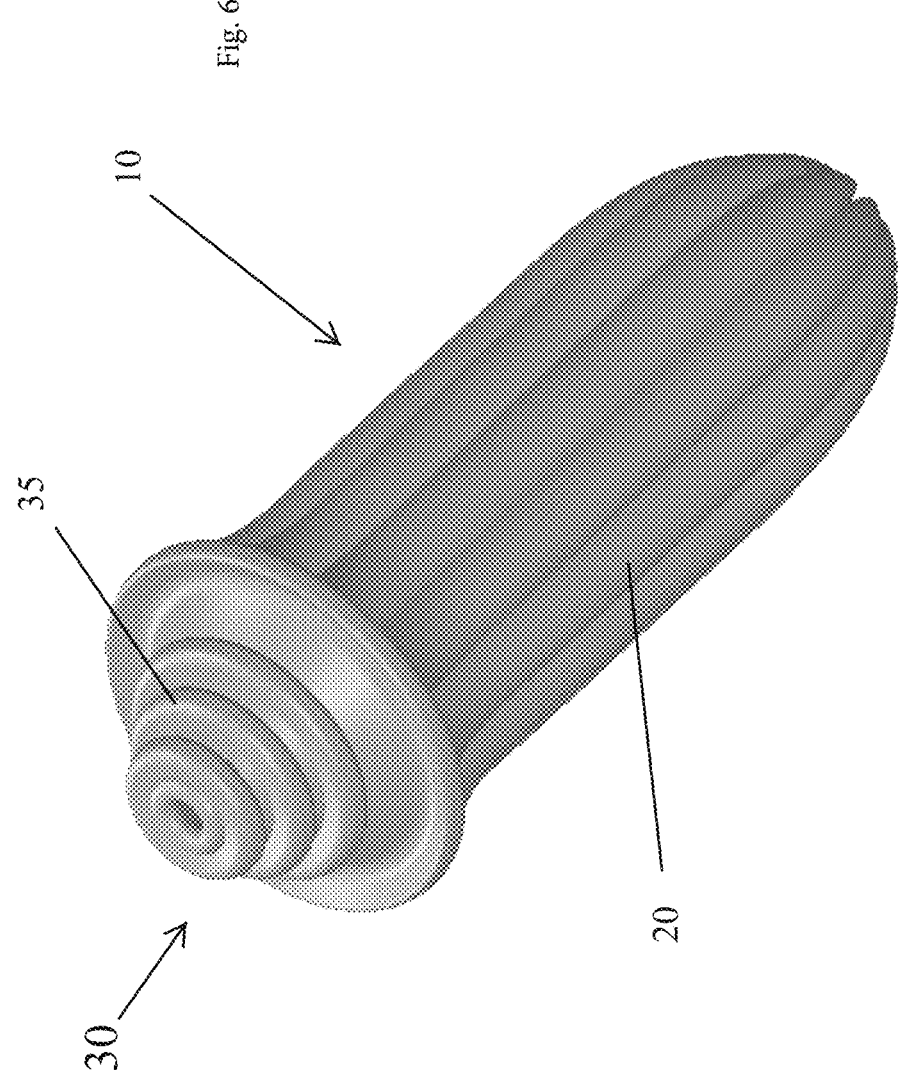
FIG. 6 is a preferred embodiment of the present invention.

FIGS. 1, 5 and 6 show views of various preferred embodiments of the present invention, designated generally by the number 10. In a preferred embodiment, plug 10 can include main member 20 and tip 30. In a preferred embodiment, plug 10 is inserted into a user's vagina and protects the vagina/vaginal canal 40, by among other things, preventing foreign or non-foreign substances from getting into the vagina 40, which in turn can prevent infections in the vagina 40. Plug 10 can also act as an odor blocker when inserted into the vagina. In a preferred embodiment, plug 10 can be temporarily inserted into a user's vagina. Tube or main member 20 can be hollow or solid or partially hollow.

Figure 2:
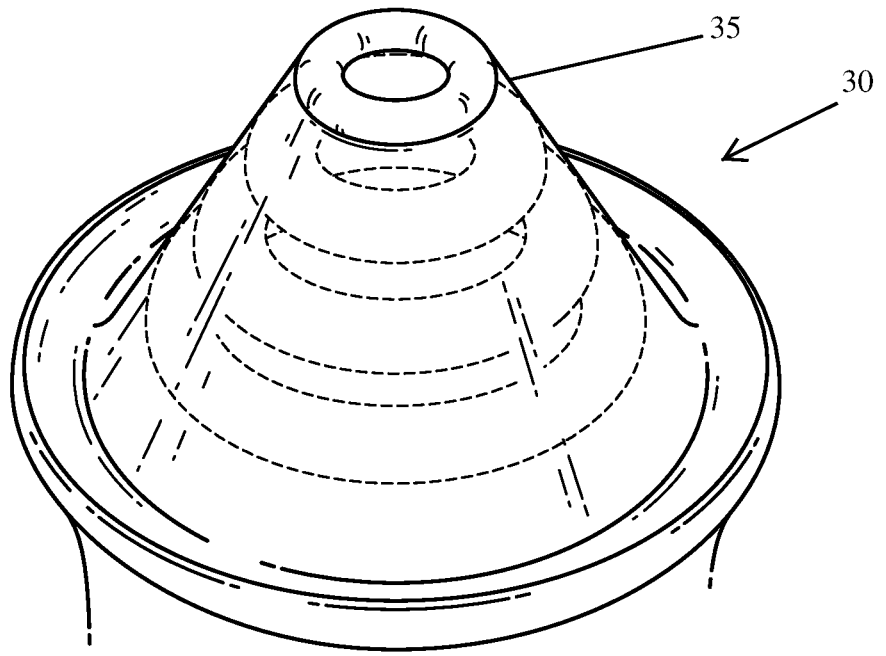
FIG. 2 is a lateral view of a preferred embodiment of the tip of the present invention.
Figure 3:
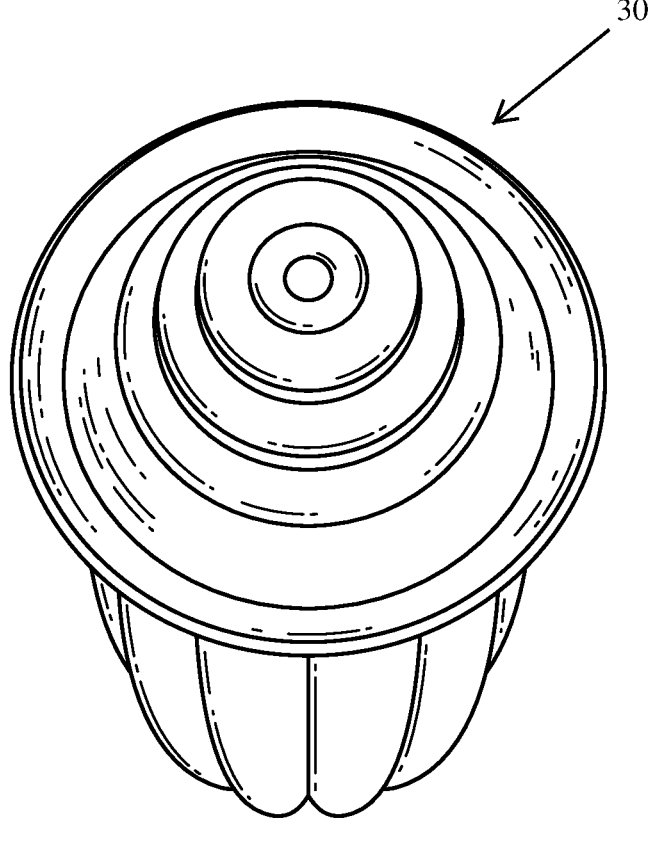
FIG. 3 is a top view of a preferred embodiment of the tip of the present invention.

FIGS. 2 and 3 show views of various preferred embodiments of tip or end member 30 of the present invention. In a preferred embodiment, tip 30 can have rings or ridges 35 that preferably provide a grip and/or better traction when the device or plug 10 is inserted or removed from a user's vagina 40. End member 30 preferably aids in grip for a user and/or traction in the event the device or plug 10 is being used in water, with a slippery substance or if the insertion or removal of the device is being done with a gloved hand.

Figure 4:
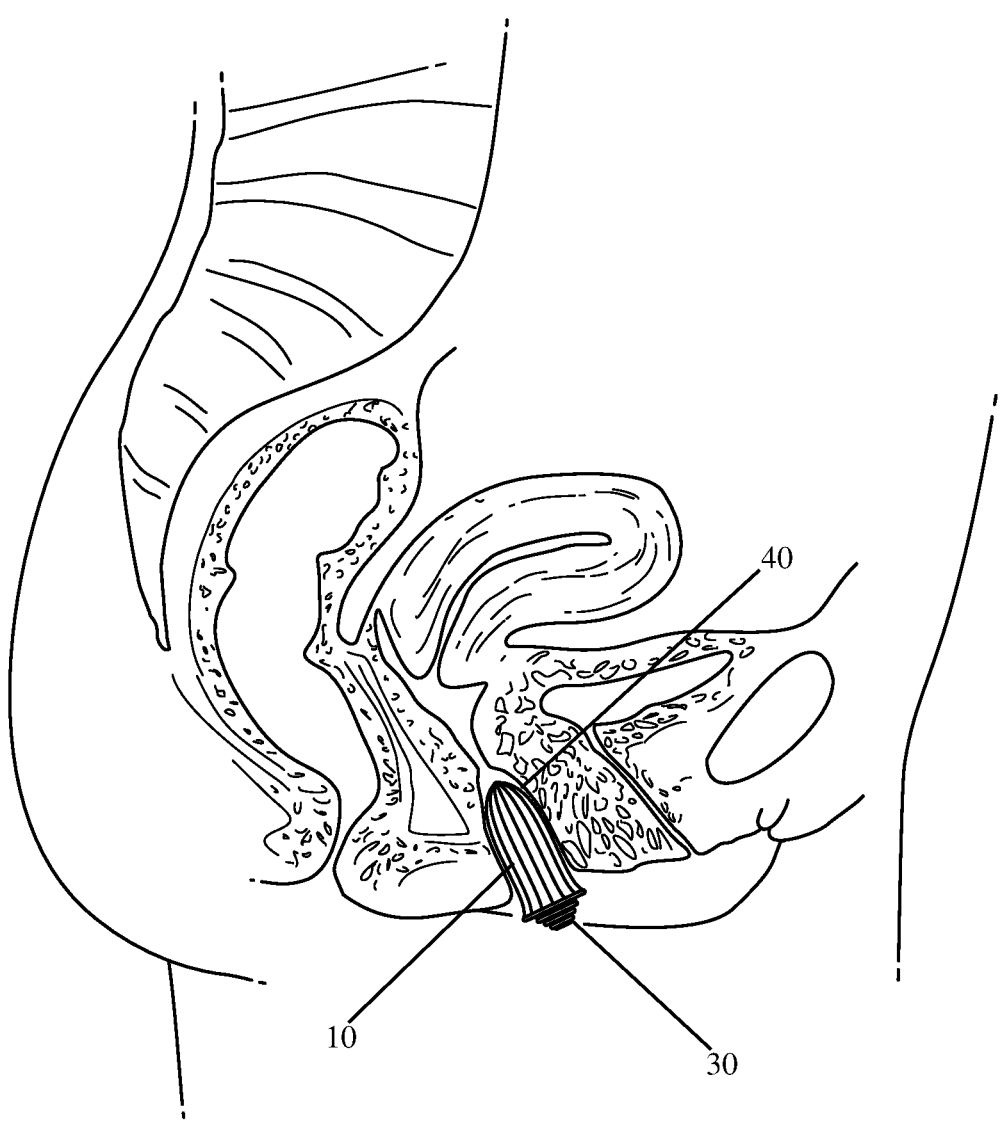
FIG. 4 is a sagittal/lateral view of a preferred embodiment of the present invention inserted into the vagina/vaginal canal in relation to other parts/organs of the body.

FIG. 4 shows plug 10 inserted in a user's vagina 40. In a preferred embodiment, the tube 20 is about the same length and width of the user's vagina/vaginal canal necessary to provide a snug fit but not too snug to cause irritation and non-functionality. In a preferred embodiment, first member 20 extends vertically from just below the user's cervix and extends just outside the opening of the vagina 40. FIG. 4 shows tip 30 extending just beyond the opening of the vagina 40, and does not cause irritation to the user.

FIGS. 1, 5, and 6 show a preferred embodiment of the present invention which has rounded end 25 of tube 20. Rounded end 25 preferably prevents injury to the cervix in case the top-most portion of plug 10 accidently comes in contact with the cervix of a user.

In a preferred embodiment of the present invention, tip 30 is flexible. In a preferred embodiment of the present invention, tip 30 has ridges and is collapsible and can invert inside the interior of tube 20 for ease of use and comfort. In a preferred embodiment of the present invention, inverted tip 30 preferably prevents rubbing of the initially extroverted tip along the panty line.

In a preferred embodiment of the present invention, plug 10 has a bell-like shape, wherein rounded end 25 is broader than tip 30.

In a preferred embodiment of the present invention, plug 10 can be made of medical grade silicone as approved by the Food and Drug Administration (FDA) and can come in various sizes and colors, including but not limited to magenta, yellow, blue, pink, etc.

In a preferred embodiment of the present invention, plug 10 is made of biocompatible material(s).

In a preferred embodiment of the present invention, tip or insertion tool 30 preferably has small grooves and or spirals 35 to add traction to ensure proper placement in the vaginal canal and allow for precise control over use of the plug 10.

In various preferred embodiments of the present invention, plug 10 preferably varies in size to accommodate shallow and deep vaginal canals and can be sized and shaped to accommodate any dimensions of a vaginal canal.

In a preferred embodiment of the present invention, plug 10 preferably comes with a plastic carrying case with small holes for ventilation.

The following is a list of parts and materials suitable for use in the present invention:

| PARTS LIST: | |
| --- | --- |
| PART NUMBER | DESCRIPTION |
| 10 | plug/device |
| 20 | first member/main member/tube |
| 25 | rounded end |
| 30 | tip/end member/insertion tool |
| 35 | rings/ridges/grooves/spirals |
| 40 | vagina |

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. A method of preventing entry of a foreign substance, such as wax, into a vagina during a waxing procedure, the method comprising inserting a device into the vagina prior to the waxing procedure, wherein the device comprises:

a. a tube sized and shaped to fit inside the vagina, wherein the tube has two ends located opposite from one another, a first end having a substantially rounded shape, and a second end;

b. wherein said second end is sized and shaped to cover the opening of the vagina and comprises concentric circle ridges or grooves that aid as a grip and allow for insertion and placement of the tube inside the vagina with said second end extending outside of the vagina;

c. wherein said outer surface of said second end is pyramidal in shape to act as a grip and help with insertion and placement of the tube into the vagina; and d. wherein said tube has a uniformly shaped exterior surface that extends from the first end to the second end, wherein there are straight grooves on the exterior surface that extend longitudinally and cover the entirety of the exterior surface.

2. The method of claim 1, wherein the device is made out of a biocompatible material.

3. The method of claim 1, wherein the second end of the tube is flexible.

4. The method of claim 1, wherein the second end is not collapsible into the tube.

5. A method of protecting a vaginal area during a waxing procedure using a vaginal plug, the method comprising inserting the vaginal plug into the vagina prior to the waxing procedure, wherein the vaginal plug comprises:

a. a tube sized and shaped to fit snugly inside a vaginal canal, said tube having a grooved exterior surface and wherein the grooves extend the entire length of the tube; and b. an insertion tip pyramidal in shape located at one end of the tube, wherein said tip is sized and shaped to cover the opening of the vaginal canal, and extends outside of the vaginal canal, said tip having an outer surface wherein said outer surface has concentric circle grooves that act as a grip to help with insertion and placement of the plug into the vaginal canal.

6. The method of claim 5, wherein the plug is made out of a biocompatible material.

7. The method of claim 5, wherein the insertion tip is not collapsible into the tube.

8. A method of protecting a vagina from a substance during a pubic hair removal procedure, the method comprising inserting a device into the vagina prior to the pubic hair removal procedure, wherein the device comprises:

a. a tube, sized and shaped to fit inside the vagina, wherein the tube has two ends located opposite from one another, a first end having a generally rounded shape, and a second end, and wherein said tube has an exterior surface and grooves on the exterior surface that extend longitudinally from end to end and cover the entirety of the exterior surface;

b. said second end having an outer surface and sized and shaped to cover the opening of the vagina; wherein said second end acts as a tool to allow for insertion and placement of the tube inside the vagina with said second end extending outside of the vagina;

c. wherein said second end is pyramidal in shape to aid with insertion and placement of the device into the vagina; and d. wherein said outer surface of said second end includes concentric ridges that also aid in being a grip to help with insertion and placement of the tube inside the vagina and removal of the tube from the vagina.

9. The method of claim 8, wherein the device is made out of a biocompatible material.

10. The method of claim 8, wherein the second end does not collapse into the main member.

11. The method of claim 1, wherein the tube has a bell-like shape.

12. The method of claim 1, wherein the tube extends vertically from just below a cervix and extends just outside the opening of the vagina.

13. The method of claim 5, wherein the tube has a uniformly shaped exterior surface that extends from the tip.

14. The method of claim 5, wherein the tube has a bell-like shape.

15. The method of claim 5, wherein the grooved exterior surface extends from the insertion tip to the second end of the tube.

16. The method of claim 8, wherein the tube exterior surface is uniformly shaped and extends from the first end to the second end.

17. The method of claim 8, wherein the grooves extend from the second end to the bottom of the first end of the tube.

18. The method of claim 1, wherein the grooves extend from the second end to the bottom of the first end of the tube.

\* \* \* \* \*